(12) United States Patent
Lee et al.

(10) Patent No.: US 9,867,551 B2
(45) Date of Patent: Jan. 16, 2018

(54) LOCATING SYSTEM FOR LOCKING HOLE OF INTRAMEDULLARY NAIL

(71) Applicants: National Chiao Tung University, Hsinchu (TW); National Taiwan University Hospital Hsin-Chu Branch, Hsinchu (TW)

(72) Inventors: Meng-Shiue Lee, Hsinchu (TW); Sung-Yueh Wu, Hsinchu (TW); Wensyang Hsu, Hsinchu (TW); Tze-Hong Wong, Hsinchu (TW); Tien-Kan Chung, Hsinchu (TW); Chia-Pei Wu, Hsinchu (TW)

(73) Assignees: NATIONAL CHIAO TUNG UNIVERSITY, Hsinchu (TW); NATIONAL TAIWAN UNIVERSITY HOSPITAL HSIN-CHU BRANCH, Hsinchu (TW)

( * ) Notice: Subject to any disclaimer, the term of this patent is extended or adjusted under 35 U.S.C. 154(b) by 481 days.

(21) Appl. No.: 14/476,353

(22) Filed: Sep. 3, 2014

(65) Prior Publication Data

US 2015/0245786 A1    Sep. 3, 2015

(30) Foreign Application Priority Data

Mar. 3, 2014    (TW) ............................. 103107101 A

(51) Int. Cl.
| | |
|---|---|
| A61B 5/05 | (2006.01) |
| A61B 5/06 | (2006.01) |
| A61B 5/00 | (2006.01) |
| A61B 17/17 | (2006.01) |

(52) U.S. Cl.
CPC ............ *A61B 5/062* (2013.01); *A61B 5/4504* (2013.01); *A61B 5/746* (2013.01); *A61B 17/1707* (2013.01); *A61B 17/1725* (2013.01)

(58) Field of Classification Search
CPC combination set(s) only.
See application file for complete search history.

(56) References Cited

U.S. PATENT DOCUMENTS

| | | |
|---|---|---|
| 5,049,151 A | 9/1991 | Durham et al. |
| 5,411,503 A | 5/1995 | Hollstien et al. |

(Continued)

*Primary Examiner* — Ellsworth Weatherby
(74) *Attorney, Agent, or Firm* — Haynes and Boone, LLP

(57) ABSTRACT

The present invention discloses a two-stage locating device and the method thereof. In stage-one, the preliminary locating device finds the approximate area of the locking hole encircled with the magnetic material on the intramedullary nail. In stage-two, the pinpoint device has a plurality of targeting devices and includes a transparent plate with a plurality of alignment lines. According to the deviations between each pointing device and the alignment lines, the direction of the pinpoint device for further adjustment can be determined. The present invention can determine the position and the orientation of the locking hole on the intramedullary nail quickly and precisely to shorten the time spent to implant the intramedullary nail. Furthermore, the present invention can also have a conductive circuit to connect to an alarm device. Thus, the precise location can be determined through the different alarm signals based on the contact conditions between each directing devices and the conductive circuit.

7 Claims, 16 Drawing Sheets

(56) References Cited

U.S. PATENT DOCUMENTS

| | | | |
|---|---|---|---|
| 5,514,145 A * | 5/1996 | Durham | A61B 17/1707 |
| | | | 408/115 R |
| 6,162,228 A | 12/2000 | Durham | |
| 6,387,096 B1 * | 5/2002 | Hyde, Jr. | A61B 17/68 |
| | | | 606/60 |
| 7,753,913 B2 | 7/2010 | Szakelyhidi, Jr. et al. | |
| 2005/0075562 A1 * | 4/2005 | Szakelyhidi, Jr. | A61B 5/06 |
| | | | 600/424 |
| 2009/0306665 A1 * | 12/2009 | Lerner | A61B 17/1703 |
| | | | 606/64 |

* cited by examiner

LOCATING SYSTEM FOR LOCKING HOLE OF INTRAMEDULLARY NAIL

RELATED APPLICATIONS

This application claims the benefit of Taiwan Patent Application No. 103107101, filed on Mar. 3, 2014, at the Taiwan Intellectual Property Office, the entire disclosure of which is incorporated herein by reference.

FIELD OF THE INVENTION

The present invention discloses a system including two location apparatuses for the intramedullary nail and a location method thereof and specifically refers to the location apparatuses for a locking hole of an intramedullary nail and a location method thereof which are applied to a two-stage location procedure. The location apparatus takes advantages of the force at a distance generated from magnetic fields or electromagnetic fields to detect the position and the orientation of the locking hole of an intramedullary nail.

BACKGROUND OF THE INVENTION

At present, An intramedullary nail is the main method to fix a fractured long bone to let it heal at present. As shown in FIG. 1, the basic structure of the intramedullary nail includes a long intramedullary nail 11 having an intramedullary nail locking hole 12, and a locking screw 22 corresponding to the intramedullary nail locking hole 12. In the processes to re-connect a broken portion 13 of the long bone 14 and to fasten the intramedullary nail 11, the locking screw 22 has to pass through the intramedullary nail locking hole 12 on the intramedullary nail 11, and has to be locked at one end of the fractured long bone 14. In the situation that the intramedullary nail 11 cannot be seen, it is usually the most time-consuming step in the whole processes to find the exact position and the orientation of the intramedullary nail locking hole 12 which is already inserted into the interior of the long bone 14.

In clinical situations, there are two methods to locate the intramedullary nail locking hole. The first method uses a parallel mechanism to assist in determining the location. The method takes one end of the intramedullary nail that is not inserted into the long bone marrow as a reference point, which is connected to a parallel mechanism to guide to the location. However, the intramedullary nail is forced during the surgery, and thus it is easy for it to be deformed or twisted. For that reason, a location error to the intramedullary nail locking hole can easily be made. Hence, this method is not suitable to a situation where the intramedullary nail locking hole is inserted into the deep interior of long bone marrow. The other method uses X-ray imaging to assist in the location. The photograph of long bone is taken by X-ray, and then the position of the intramedullary nail locking hole in the long bone can be observed directly on the photograph. However, this method causes the patients and the medical personnel to be exposed to radiation, and it causes concern that this method may jeopardize the health of the medical personnel who frequently use this method frequently.

Most location methods without radiation in the prior art can only find the position of intramedullary nail locking hole, but cannot quickly determine the accurate orientation of the intramedullary nail locking hole. Taking the optical location method as an example, a light source is inserted from the end of the intramedullary nail locking hole that does not enter the long bone marrow. When the light source is put at the place near the intramedullary nail locking hole, the light from the light source can be emitted through the intramedullary nail locking hole and through the bone, the tissue and the skin. Finally, a light spot can be seen on the surface of the limb of the patients. The advantage of this location method is that it can be performed quickly, but the disadvantage thereof is that the light spot becomes too large after passing through the tissue and the skin to determine the accurate position and orientation of the intramedullary nail locking hole due to the diffusion of the light spot.

Apart from this, the methods disclosed by the patents that apply the principle of magnetics as the location method are still unable to locate the position and the orientation of the locking hole. For example, a location method disclosed in U.S. Pat. No. 5,411,503 is that during the location procedure, two electromagnets are inserted into the intramedullary nail, and are conducted with the alternating current to generate two alternating electromagnetic fields. The coils aligned in perpendicular to one another outside the intramedullary nail are used to induct the alternating electromagnetic fields. When the induction current in the coils is zero, the location procedure is completed. In this method, the device with high intensity current has to be placed into the body. That causes a safety risk of electric shock. Furthermore, it is necessary to use four outer coils in this method. However, the magnetic fields generated by these outer coils interfere with one another, which could lead to a location error. In addition, during the location procedure, the proper adjustment direction to the location device cannot be obtained. The reduction of the location time is limited due to the trial and error steps that are necessary with this method.

U.S. Pat. No. 5,049,151 discloses an intramedullary nail equipped in its interior with a permanent magnet, and its location device is a magnet set on a universal joint to freely rotate. When the location device gets close to the permanent magnet inside the intramedullary nail, the magnet on the location device is attracted to complete the location procedure. However, in fact, when only a single magnet is adopted in the location device, the given direction only represents the gradient direction of the magnetic field of the permanent magnet. That is not the necessary direction in which the long bone should be drilled. Furthermore, when the single magnet on the location device is attracted by the permanent magnet onto the surface of the long bone, the direction of the single magnet also fails to identify the direction which should be followed to drill. There is still a problem to locate the orientation of the locking hole because the direction which should be followed may not be vertical to the surface of the long bone where the single magnet is attracted.

U.S. Pat. No. 5,514,145, similar to U.S. Pat. No. 5,049,151, discloses that a single magnet is set on a universal joint and an additional location needle. After the location procedure is completed, the location needle is launched to the long bone. However, this method also has the same disadvantages as U.S. Pat. No. 5,049,151.

U.S. Pat. No. 6,162,228 improves the position of the permanent magnet. A slender stick is inserted into an intramedullary nail from the end of the intramedullary nail outside the marrow, and a permanent magnet enters the intramedullary nail along with the slender stick. The position of the permanent magnet deviates a distance from the locking hole, and thus the permanent magnet does not prevent the drill from passing through the locking hole. That allows the bone to be drilled immediately after the location procedure is completed. However, the magnetic location device detects the magnetic field by one single outer magnetic rod as well. It is similar to U.S. Pat. No. 5,049,151 and U.S. Pat. No. 5,514,145. When the single magnetic rod is attracted by the magnetic field, the single magnetic rod indicates only the gradient direction of the magnetic field of the permanent magnet. It only determines the position of the locking hole, but cannot determine the orientation of the locking hole.

In U.S. Pat. No. 7,753,913, an active magnetic sensor array is used, and they are arranged according to the shape of the magnetic field generated by the implanted magnet. The sensor array determines the direction of the magnetic field according to the various magnitudes of the magnetic flux in different positions. When the sensor array detects the same magnetic flux, the location procedure is completed. Operating this system is more complicated and is not direct. The reduction in location time is limited due to the trial and error steps that are necessary when using this device.

SUMMARY OF THE INVENTION

The present invention discloses a location system including a targeting apparatus. The targeting apparatus has multiple magnetic rods, which is characterized in that it is easy to determine the orientation that should be adjusted to the targeting apparatus in the locating process. In addition, the targeting apparatus can find the position and orientation of the locking hole quickly and precisely. According to the concept, the Applicant discloses the contents of the present invention as follows.

In accordance with an aspect of the present invention, a location system for a locking hole of an intramedullary nail and a location method thereof are disclosed. The system and method take advantage of magnetic location in a two-stage approach which can reduce the range to search and determine the orientation that should be adjusted to the targeting apparatus during the locating process. Thus, the position and orientation of the locking hole of the intramedullary nail can be determined precisely. The system includes:

An intramedullary nail: the intramedullary nail disclosed in the present invention has a special locking hole. The locking hole is circled with magnetic material in which the directions of the poles in the magnetic material are parallel to the entrance direction of the locking screw. After the intramedullary nail is implanted into the intramedullary of a long bone, the location is performed. After the location, the drilling can be immediately performedusing the lock and connection between the locking screw and the locking hole of the intramedullary nail, the fracture of the long bone can be fixed with the intramedullary nail.

Preliminary locating apparatus: this is composed of an elastomer having a locating hole and a plurality of magnets fastened with the elastomer around the locating hole. The plurality of magnets are used to quickly look for the approximate range of the magnetic material circling the locking hole to reduce the search area to the following location.

Pinpoint apparatus: this is composed of a transparent bearing plate and a plurality of pointing devices including the magnetic rods, wherein the transparent bearing plate has alignment lines corresponding to the pointing devices to determine the position and the orientation of the locking hole of the intramedullary nail. During location with the pinpoint apparatus, the orientation that should be adjusted to the pinpoint apparatus can be determined to reduce the search time to the location.

In accordance with another aspect of the present invention, a magnetic targeting apparatus is disclosed. The magnetic targeting apparatus includes: (A) a transparent bearing plate having a top surface, a bottom surface, and three containing through holes equally distant from one another extending from the top surface to the bottom surface, each of which is divided into an upper section, a lower section, and a middle section having a diameter larger than that of the lower section, and three pointing devices, each of which includes: (A1) a spherical embedded portion disposed in the middle section of the respective containing through hole; (A2) a first pointing end having one magnetic pole, passing through the upper section of the respective containing through hole, and connected to the spherical embedded portion; (A3) a second pointing end having the other magnetic pole, passing through the lower section of the respective containing through hole, coaxial with the first pointing end, and connected to the spherical embedded portion; and (A4) a conductive layer covering the spherical embedded portion, the first pointing end and the second pointing end; (B) a first conductive circuit disposed on the transparent bearing plate and electrically coupled to the conductive layer; and (C) a transparent positioning plate disposed on the transparent bearing plate in parallel, having three positioning through holes and including: (C1) a height adjuster that adjusts the height as measured from the transparent bearing plate to the transparent positioning plate; (C2) three hole walls defining the three positioning through holes, which correspond to the three containing through holes respectively, and each of which passes therethrough a respective one of the first pointing ends and the second pointing ends; and (C3) a second conductive circuit having three tubular conductors electrically coupled to one another and disposed on the three hole walls respectively.

In accordance with a further aspect of the present invention, a magnetic targeting apparatus is disclosed. The magnetic targeting apparatus includes: (A) a bearing component having a first surface, a second surface opposite to the first surface, and three containing through holes extending from the first surface to the second surface; and (B) three pointing devices, each of which includes: (B1) a spherical portion embedded in the respective containing through hole; (B2) a first pointing end having a first magnetic pole and protruding from the spherical portion to the first surface; and (B3) a second pointing end having a second magnetic pole and protruding from the spherical portion to the second surface.

In accordance with yet another aspect of the present invention, a magnetic targeting apparatus is disclosed. The magnetic targeting apparatus includes: (A) a positioning ring having an exterior surface; (B) a plurality of pointing devices coplanar with the positioning ring, and each of which includes: (B1) a ball-joint bearing portion having a through hole with a symmetrical axis, and a ball-like space having a center located on the symmetrical axis; and (B2) a ball-joint embedded portion which has a ball-like body embedded in the ball-like space and passing therethrough a magnetic rod passing through the through hole; and (C) a plurality of connecting shafts, each of which has a first end connected to the positioning ring and a second end portion pivotally connected to the respective pointing device.

The above objects and advantages of the present invention will become more readily apparent to those ordinarily skilled in the art after reviewing the following detailed descriptions and accompanying drawings, in which:

DETAILED DESCRIPTION OF THE PREFERRED EMBODIMENTS

The present invention will now be described more specifically with reference to the following embodiments. It is to be noted that the following descriptions of preferred embodiments of this invention are presented herein for the purposes of illustration and description only; they are not intended to be exhaustive or to be limited to the precise form disclosed.

Figure 3A:
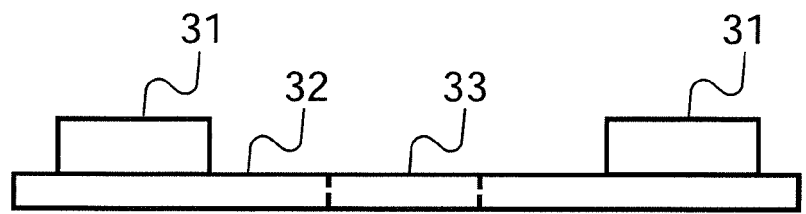
FIG. 3A is the side view of the preliminary locating apparatus of the present invention.
Figure 3B:
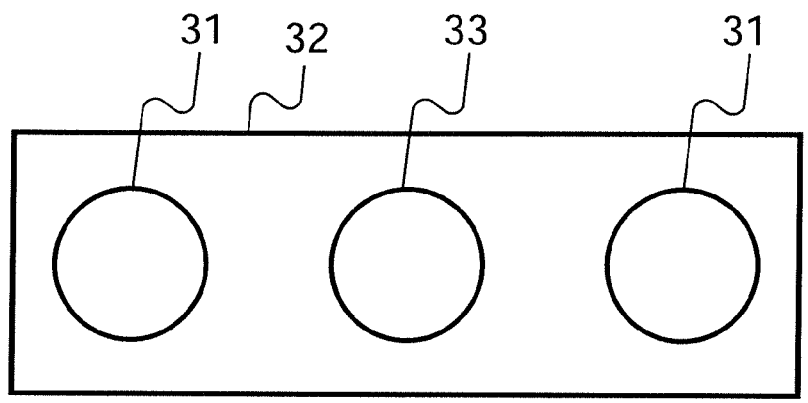
FIG. 3B is the top view of the preliminary locating apparatus of the present invention.
Figure 3C:
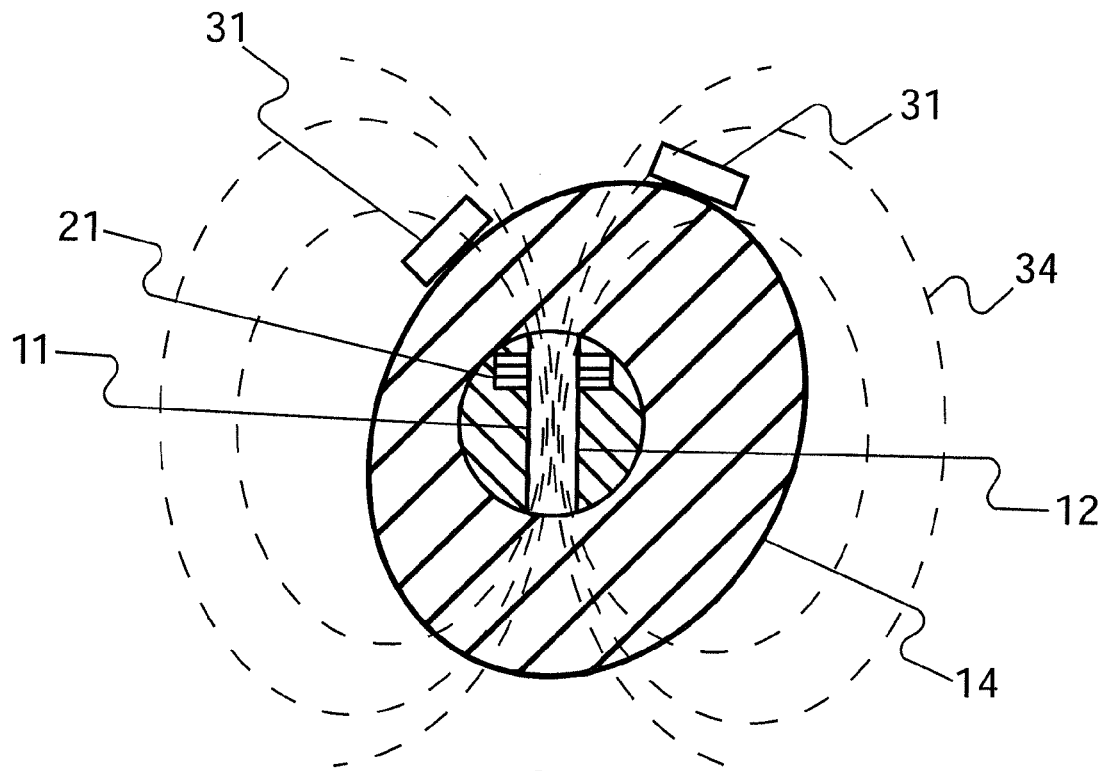
FIG. 3C is the cross-section view of the preliminary locating apparatus when it performs the stage-one location onto a locking hole circled with a magnetic material.

When the intramedullary nail 11 having the intramedullary nail locking hole 12 circled with the magnetic material 21 is implanted into the intramedullary of the long bone 14, the possible section of the long bone 14 covering the intramedullary nail locking hole 12 can be estimated by the intrinsic length of the intramedullary nail 11, and then the preliminary (stage-one) location, as shown in FIG. 3(c), is performed by the preliminary locating apparatus 30 as shown in FIGS. 3(a) and 3(b). The coupling between the magnetic field 34 generated by the plurality of magnets 31 of the preliminary locating apparatus 30 and magnetic field 34 generated by the magnetic material 21 causes the preliminary locating apparatus to target the location and stay in the same area on the long bone 14 which is to be drilled. After that, the area to be pinpointed subsequently by the pinpoint apparatus can be determined with the preliminary locating hole 33.

Figure 1:
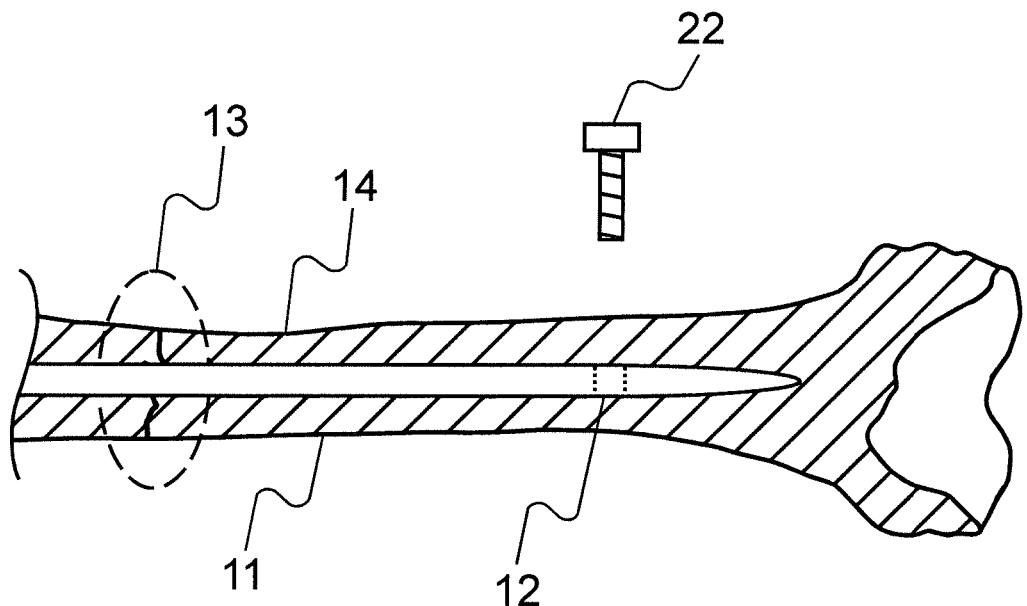
FIG. 1 shows the internal configuration of the prior art intramedullary nail.
Figure 2A:
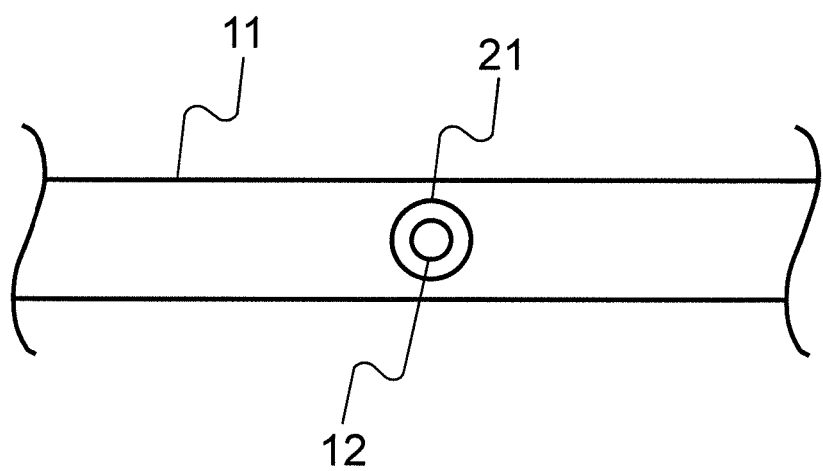
FIG. 2A shows the intramedullary nail of the present invention.
Figure 2B:
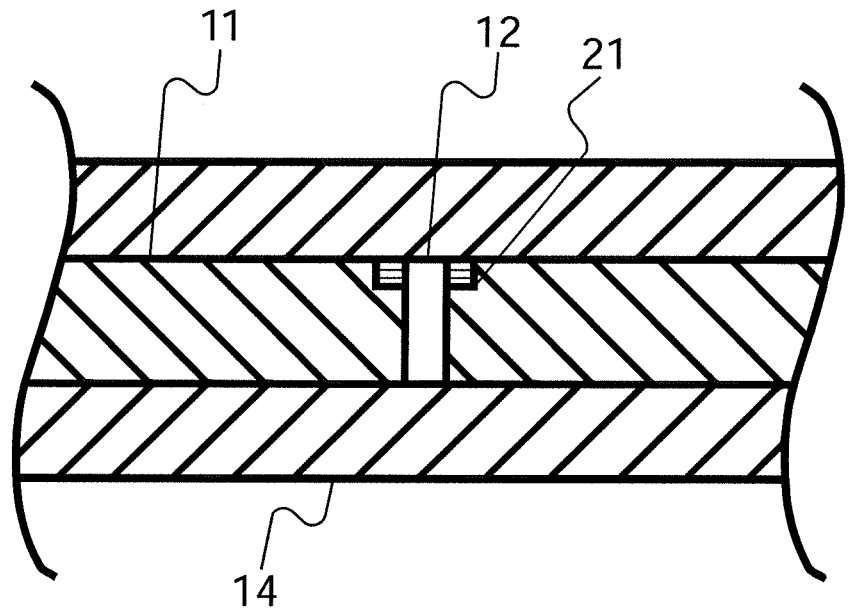
FIG. 2B and FIG. 2C are the longitudinal section views of the configurations of the intramedullary nail of the present invention.
Figure 2C:
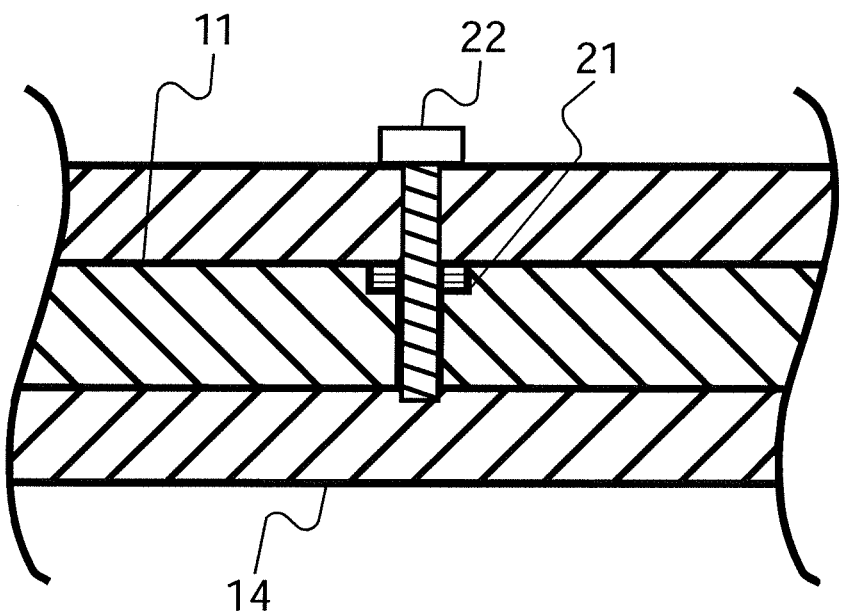
Figure 4:
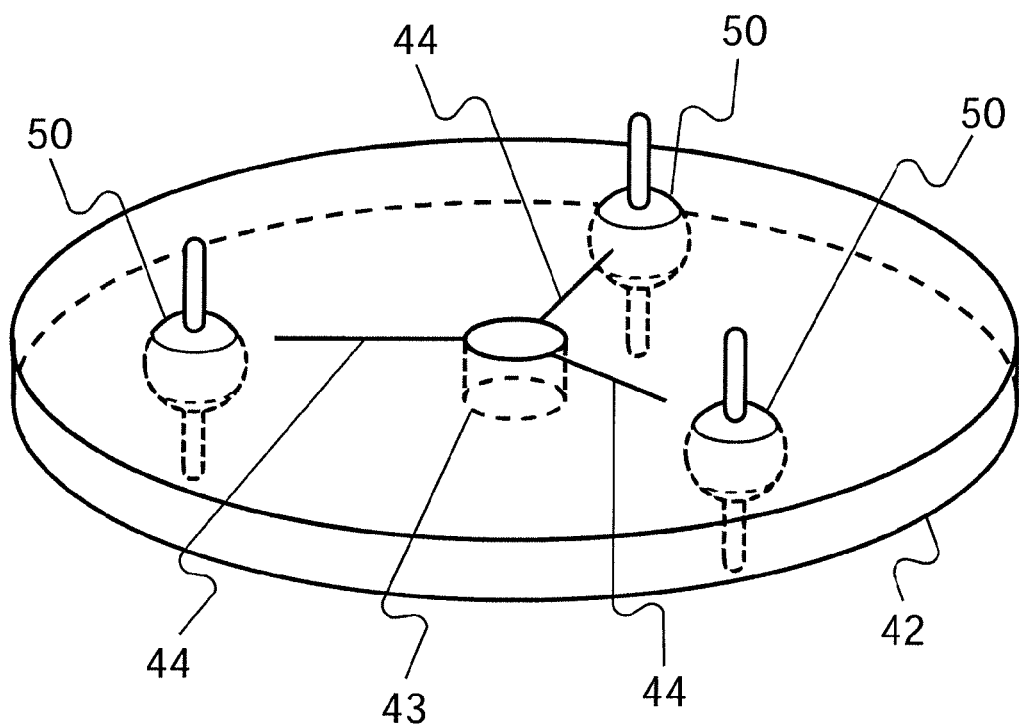
FIG. 4 shows one embodiment of the pinpoint apparatus of the present invention.
Figure 5:
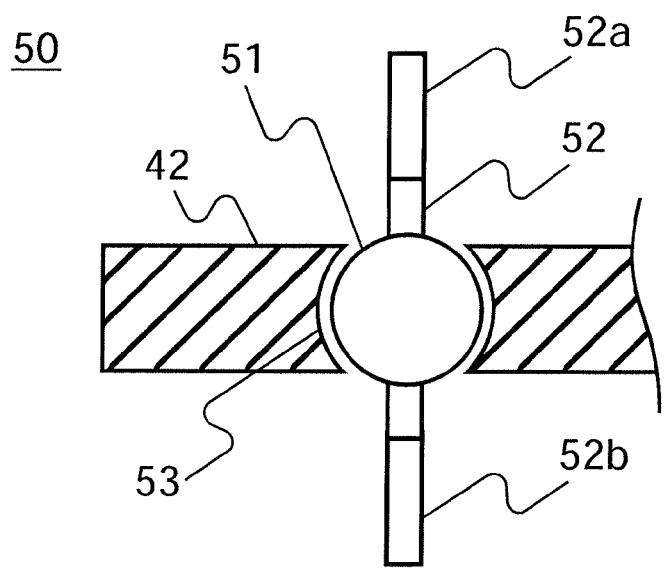
FIG. 5 is the longitudinal section view of the pointing device of one embodiment of the present invention.

The operation principle of the pinpoint apparatus can be understood by referring to FIGS. 4 and 5. The pinpoint apparatus has three identical containing through holes 53 to hold three magnetic rod type pointing devices 50. These three pointing devices 50 are installed in the same magnetic direction on a hypothetical circle on the transparent bearing plate 42, in which the center of the hypothetical circle is a through sight hole 43. The transparent bearing plate 42 is marked with three alignment lines 44 corresponding to the pointing devices 50. The user carries out the location procedure by adjusting the position and orientation of the transparent bearing plate 42 to cause each pointing device 50 to align with each corresponding alignment line 44. When the location procedure is completed, the through sight hole 43 aligns with the position and orientation of the magnetic material 21 circling the intramedullary nail locking hole 12 as shown in FIG. 2 and aligns with the position and orientation of the intramedullary nail locking hole 12. Finally, the user can drill according to the position and orientation.

FIG. 5 is the longitudinal section view of an embodiment of the pointing device. Each pointing devices 50 is composed of a spherical embedded portion 51 and a magnetic rod 52 passing through the center of the spherical embedded portion 51 and connecting to the spherical embedded portion 51. It is conducive to the location procedure that the influence of gravity is diminished by making the center of gravity of the entire pointing device 50 superimpose on the center of gravity of the spherical embedded portion 51. The spherical embedded portion 51 is embedded in the containing through hole 53 of the transparent bearing plate 42 to allow the spherical embedded portion 51 to rotate freely but not change its position. Therefore, when each pointing devices 50 enters the effective magnetic field of the magnetic material 21 circling the intramedullary nail locking hole 12, the magnetic rod 52 of each pointing devices 50 is attracted by the magnetic material 21 to cause each pointing devices 50 to swing with respect to the gravity centers of each pointing device 50. Finally, the pointing devices 50 are going to direct themselves toward the intramedullary nail locking hole 12.

Figure 6:
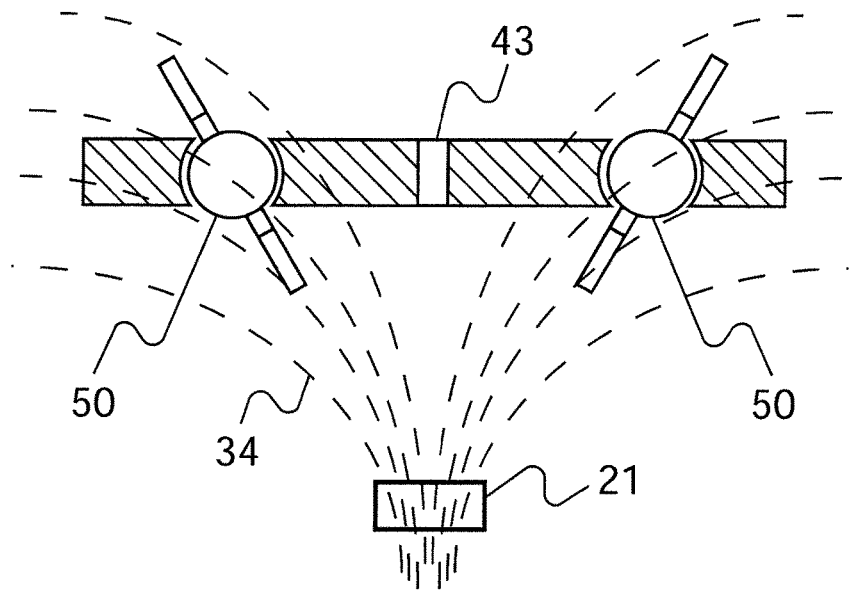
FIG. 6 is the longitudinal section view along one alignment line, the sigh hole and anyone of the rest alignment lines of an embodiment of the pinpoint apparatus of the present invention when it performs the stage-two location onto a locking hole enclosed with a magnetic material.

FIG. 6 shows the magnetic field 34 with a symmetrical axis in the surrounding space generated by the magnetic material 21 circling the intramedullary nail locking hole 12. When each pointing device 50 is influenced by the magnetic field 34 to move to the same swing angle toward the through sight hole 43 of the transparent bearing plate 42, the direction of the through sight hole 43 is the direction of the locking hole 12, which allows the locking screw 22 to screw into it.

During the location procedure, the transparent bearing plate 42 allows the user to observe the portions of the pointing devices 50 under the transparent bearing plate 42. The user can determine the adjustment position, direction and angle desired to the pinpoint apparatus by the relative directions between each pointing device 50 and each corresponding alignment line 44 to diminish the adjustment time of the location procedure.

Figure 7A:
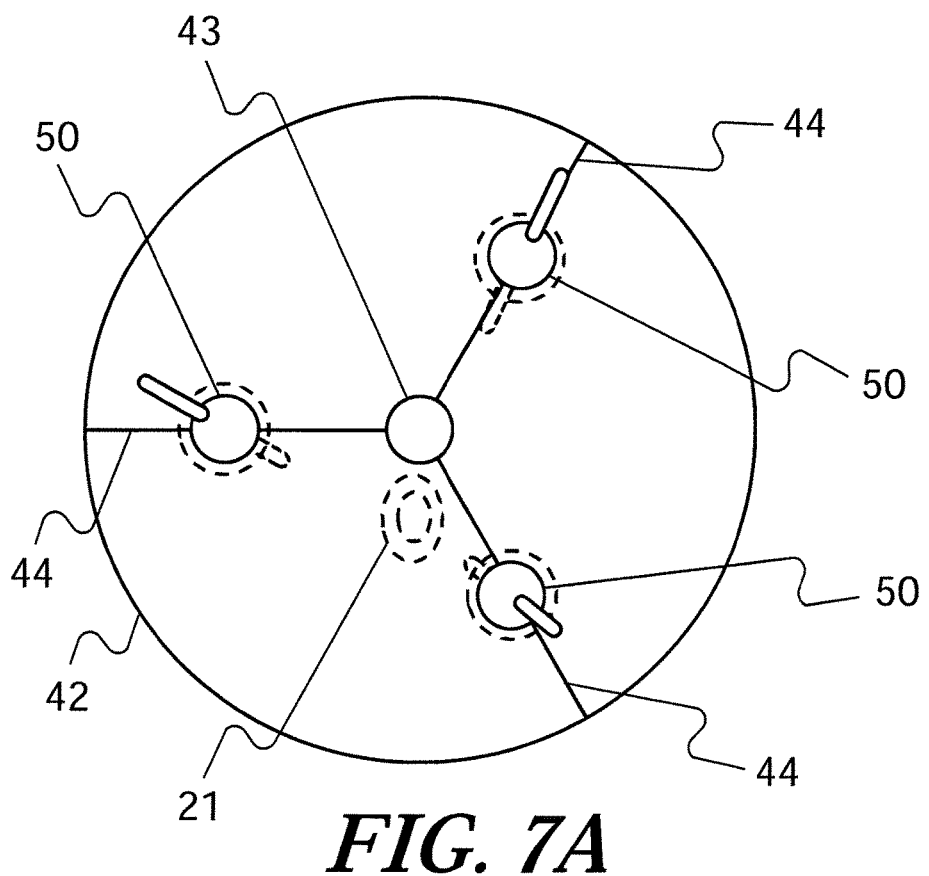
FIGS. 7A to 7C are the top views of an embodiment of the pinpoint apparatus of the present invention when it performs the stage-two location onto a locking hole enclosed with a magnetic material.
Figure 7B:
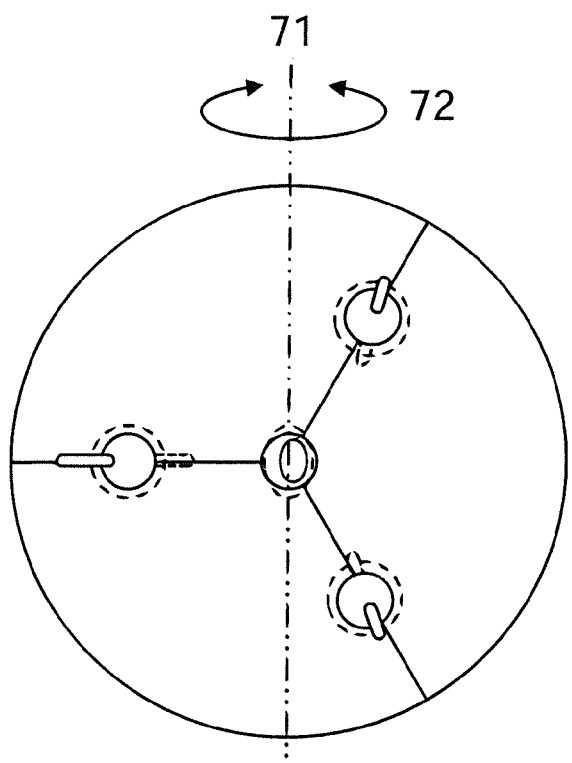
Figure 7C:
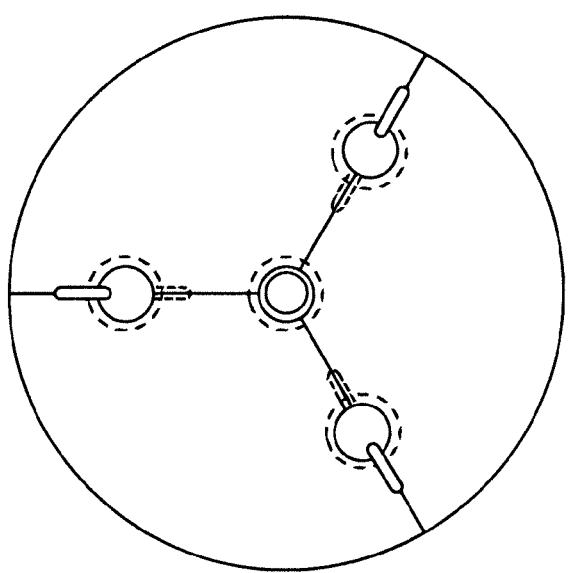

The method to determine how to adjust the position of the pinpoint apparatus is demonstrated in FIGS. 7(*a*) and 7(*b*). When each pointing devices 50 does not align with each corresponding alignment lines 44 as shown in FIG. 7(*a*), the pinpoint apparatus is moved toward the position directed by the three magnetic rods 52. When the three magnetic rods 52 approximately target the through sight hole 43, approximately align with the corresponding alignment lines 44 and cannot further align with the alignment lines 44 as shown in FIG. 7(*b*), the tilt of the pinpoint apparatus is tuned by rotating along the direction 72 with respect to the horizontal axis 71 to finely adjust the position and orientation of the pinpoint apparatus. According to the change of the swing angle of each magnetic rod 52, the position and orientation of the transparent bearing plate 42 can be adjusted to cause each magnetic rod 52 and each corresponding alignment line 44 to completely align. The steps above may have to be repeated until the through sight hole 43 is completely coaxial with the intramedullary nail locking hole 12 as shown in FIG. 7(*c*).

The function of three pointing devices can be completed by setting only two pointing devices and adjusting the transparent bearing plate 42 based on the corresponding alignment lines 44 because all the pointing devices 50 can freely rotate with respect to the transparent bearing plate 42. However, the configuration of two pointing devices increases the difficulty of the alignment and may not obtain the exact orientation of the intramedullary nail locking hole 12. The third pointing device 50 causes the extension directions of the three pointing devices to converge to form a narrow area under the transparent bearing plate 42. That allows the exact position and orientation of the intramedullary nail locking hole to be determined quickly and precisely.

This location approach is easily determines the adjustment direction which should be adopted for the pinpoint apparatus. Therefore, the position and orientation of the intramedullary nail locking hole 12 can be determined quickly and the location time can be decreased. Preferably, the weight of both ends of each magnetic rod 52 with respect to its center in the pointing devices 50 is configured to be equal. During the location procedure, it is not necessary for the pinpoint apparatus to be horizontal and it is adjustable to adapt to the position of the surgical patient to perform the location procedure in different orientations because any errors caused by gravity can be minimized because each magnetic rods 52 in the pointing devices 50 has an equal weight at both ends with respect to its center.

The pinpoint apparatus may further include an alarm device to assist with the determination of the precise location procedure with the signals in the form of sounds or lights.

Figure 8:
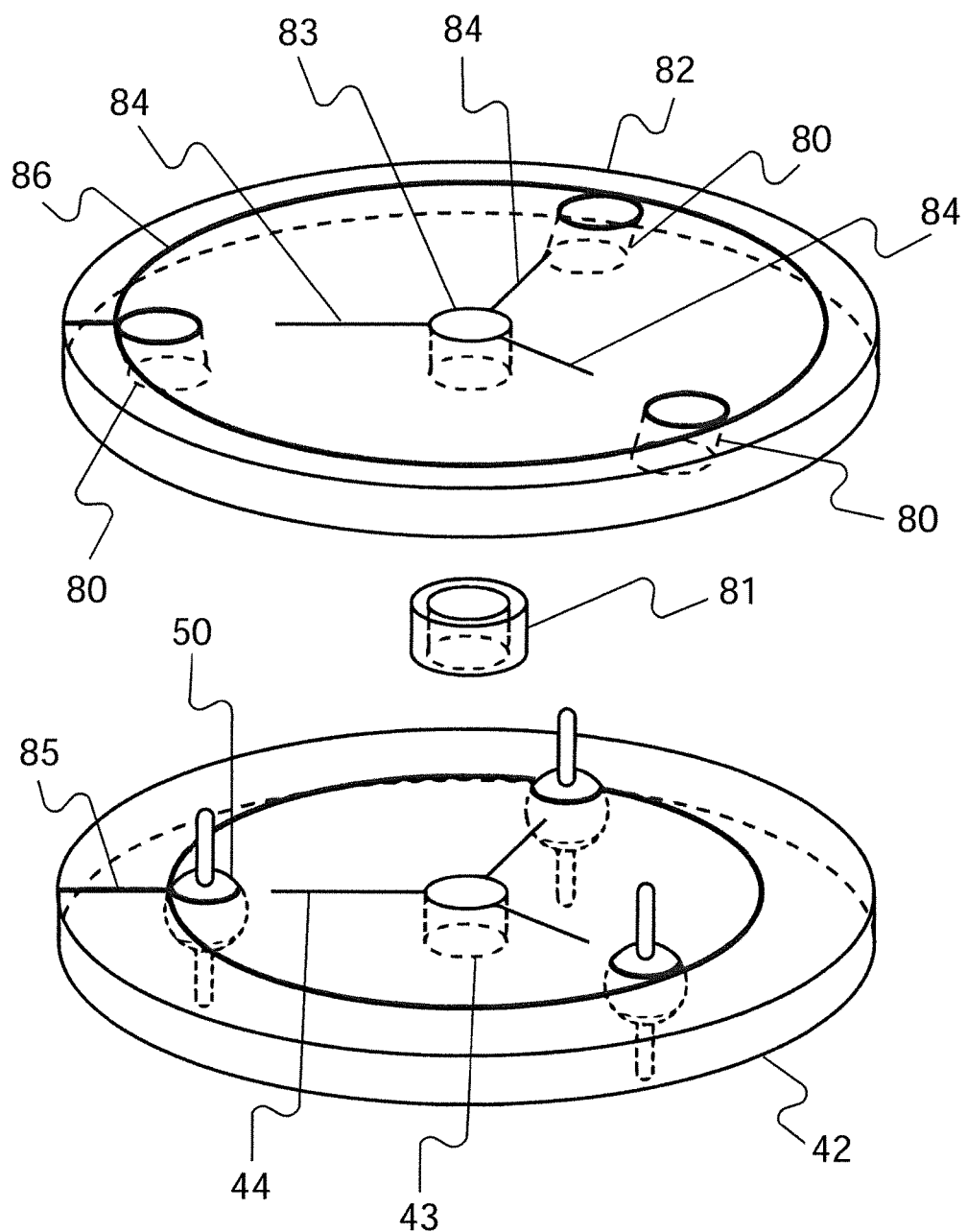
FIG. 8 shows an embodiment of the pinpoint apparatus of the present invention when it is installed with an additional alarm device.

It can be understood by referring to FIG. 8 that the configuration of the alarm device is related to the positioning plate 82 corresponding to the transparent bearing plate 42, the height adjustor 81, the first conductive circuit 85 and the second conductive circuit 86 shown in FIG. 8. The bold lines in the figure are the conductive circuits 85 and 86. The first conductive circuit 85 can be deposed on the top surface or the bottom surface of the transparent bearing plate 42. The first conductive circuit 85 always contacts each pointing device 50 which is coated with a conductive layer and the first conductive circuit 85 can be electrically coupled to the second conductive circuit 86 by the switch served by any one the pointing devices 50.

The positioning plate 82 is suitable for different height adjustors 81 with various heights to change the height between the positioning plate 82 and the transparent bearing plate 42.

It is preferable that the diameter of the through sight hole 43 matches the diameter of the corresponding through sight hole 83 of the positioning plate 82. Therefore, the positioning plate 82 should be made with transparent material because an opaque positioning plate having the diameter of the corresponding through sight hole 83 similar to the diameter of the through sight hole 43 leaves no gaps to observe the portions of the pointing devices 50 below the opaque positioning plate from the top of the entire pinpoint apparatus.

The alarm device can further include a light emitting diode (LED) and a direct-current (DC) power supply, and thus during the location procedure, the completion of the location can be determined by the on and off condition of the LED that is the result of the different conductive conditions between the first conductive circuit 85 and the second conductive circuit 86 which can be electrically coupled to any one of the pointing devices 50 coated with a conductive layer.

Figure 9A:
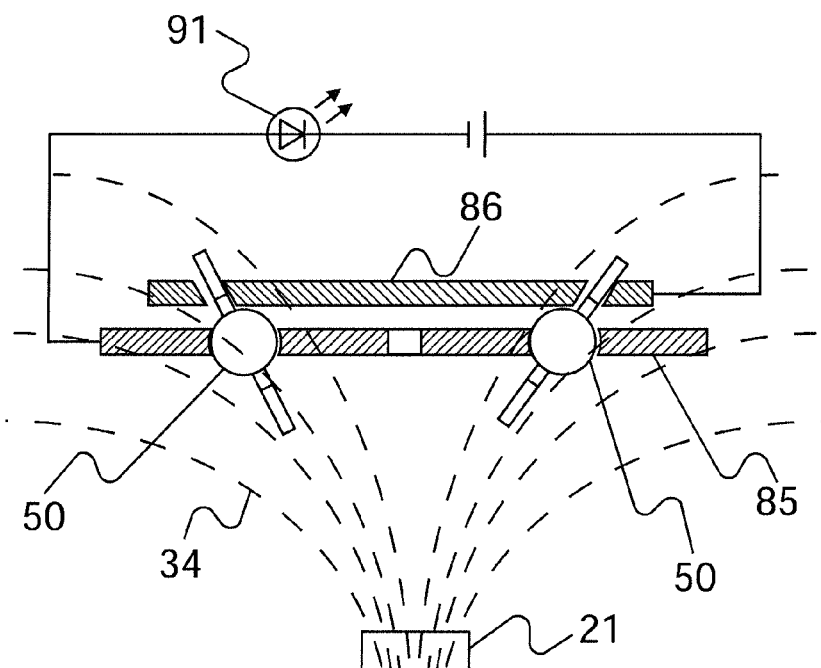
FIGS. 9A to 9C are the circuit diagrams of the alarm device of an embodiment of the present invention when it is operated to determine the location and orientation of the locking hole.
Figure 9B:
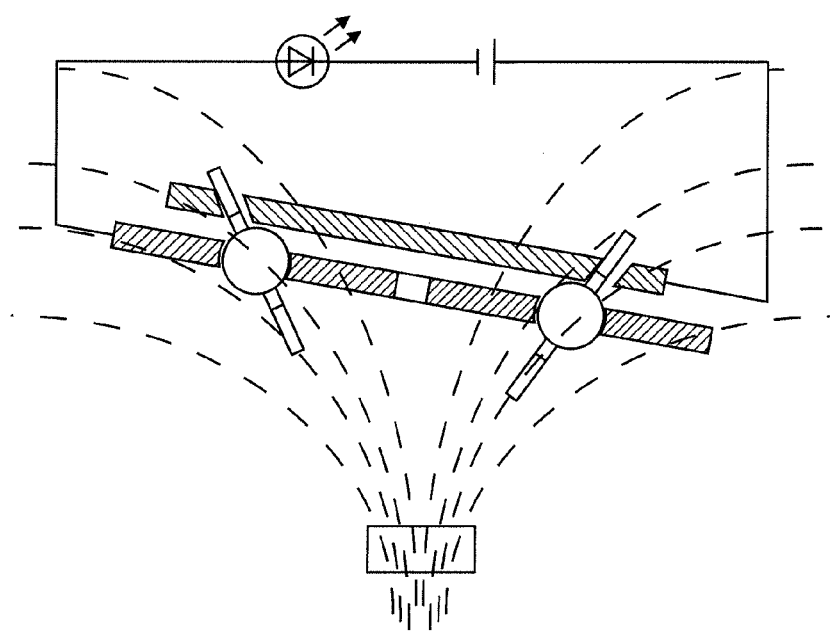
Figure 9C:
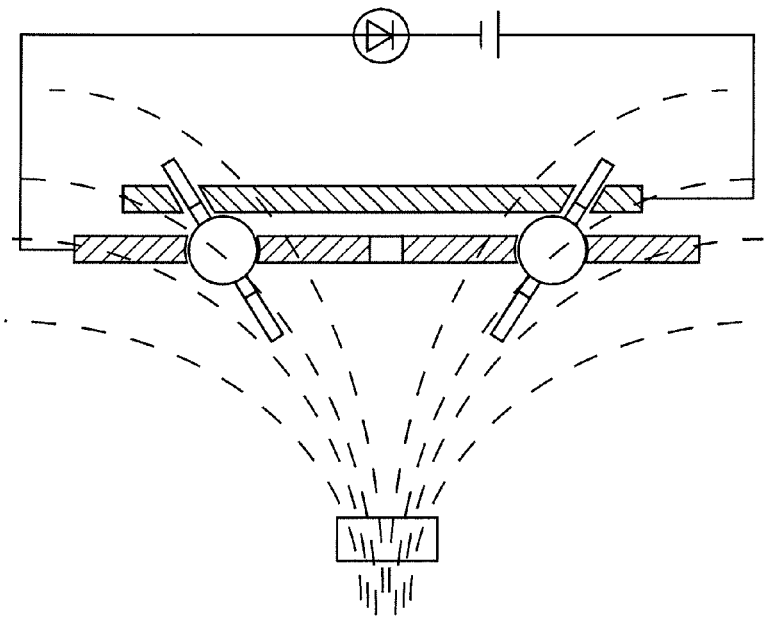

The other way to implement the second conductive circuit 86 is to make the transparent bearing plate 42 with conductive material to form the first conductive circuit 85 as shown in FIG. 9(*a*).

The way to determine the location of the alarm device is demonstrated in FIGS. 9(*a*)-9(*c*). When there is a horizontal deviation between the pinpoint apparatus and the locking hole 12, the magnetic field 34 of the magnetic material 21 deflects the pointing devices. Any one of the deflected pointing devices 50 can electrically connect to the first conductive circuit 85 and the second conductive circuit 86 to enable the alai device such as the first LED 91 as shown in FIG. 9(*a*). When there is an angular deviation between the pinpoint apparatus and the locking hole 12, at least one of the deflected pointing devices 50 can electrically connect to the first conductive circuit 85 and the second conductive circuit 86 to enable the alarm device such as the first LED 91 as shown in FIG. 9(*b*). When the location procedure is completed, all of the three magnetic rods 52 are directed to the magnetic material 21. None of the pointing devices 50 are deflected to electrically connect to the first conductive circuit 85 and the second conductive circuit 86. The alarm device such as the first LED 91 is disabled as shown in FIG. 9(*c*).

Therefore, when there is any deviation during the stage-two location procedure, the alarm device is active. When the location procedure is completed, the alarm device becomes inactive, and the intuitional alarm function is achieved. The optical alarm device shown in FIGS. 9(*a*)~9(*c*) can also be replaced by a sound alarm device.

The alarm device can further include a relay circuit 101 to cooperate with the first conductive circuit 85 and the second conductive circuit 86 to form a double alarm device. The relay circuit 101 includes LEDs to accomplish the function of the double alarm device, in which, the user can monitor the current progress of the location procedure through the signals of the different lights. The circuit diagrams are shown as FIGS. 10(*a*) and 10(*b*), in which, the first conductive circuit 85 and the second conductive circuit 86 cooperate with the alarm device and are electrically coupled to the relay circuit 101.

Figure 10A:
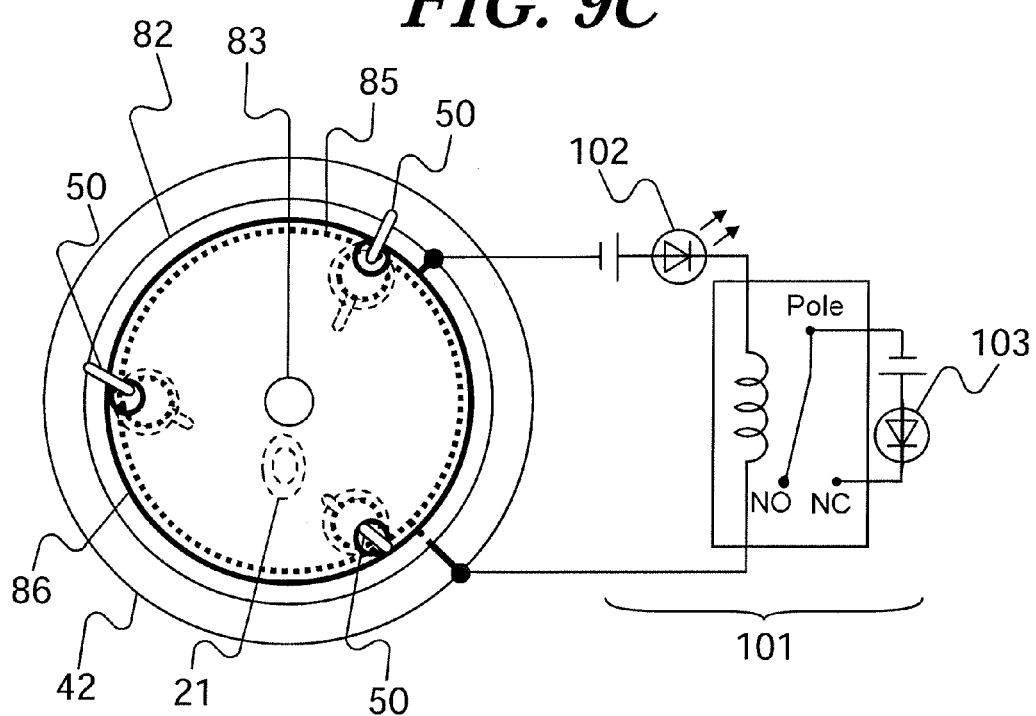
FIGS. 10A to 10C show an embodiment of the pinpoint apparatus of the present invention when it is installed with the additional alarm device and a relay circuit.
Figure 10B:
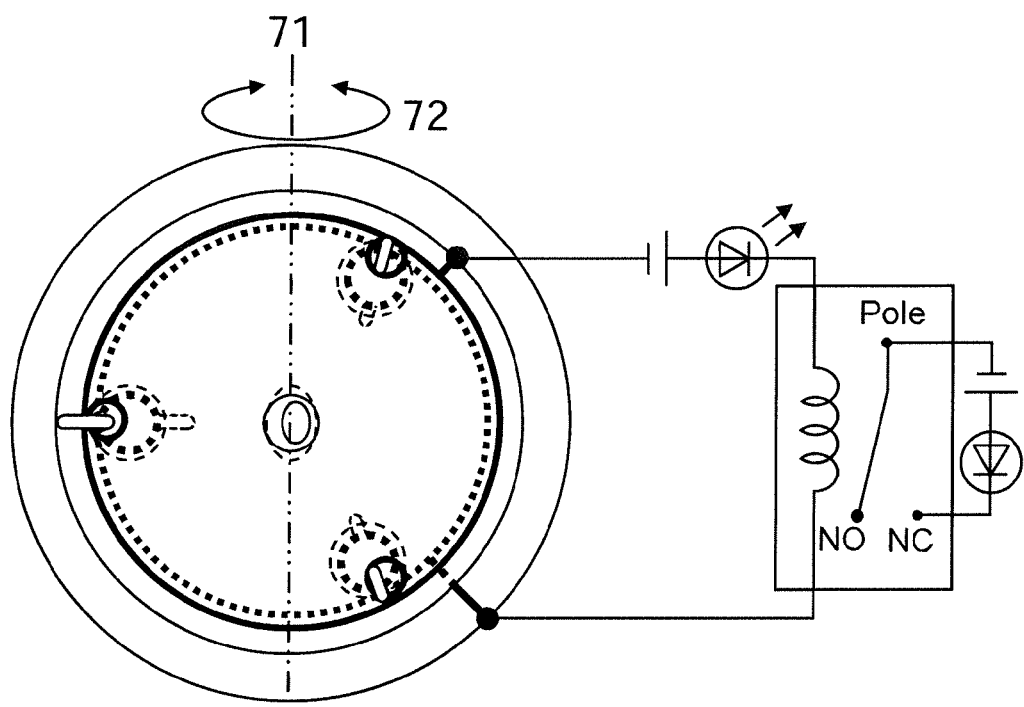
Figure 10C:
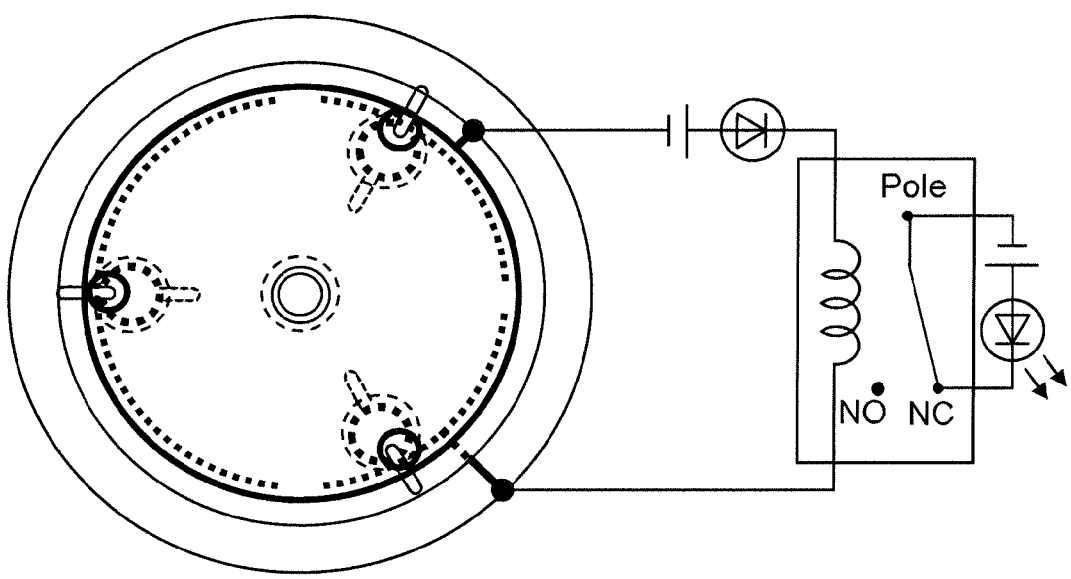

As shown in FIGS. 10(a) and 10(b), when the location procedure is still in progress, the first conductive circuit 85, the second conductive circuit 86 and the alarm device are electrically connected due to the deflection of the pointing devices 50 caused by the magnetic rods 52. Therefore, the first LED 102 is active and the second LED 103 attached to the relay is inactive. The first LED 102 provides not only the confirmation that the location procedure is not completed yet, but also the confirmation that the first conductive circuit 85 and the second conductive circuit 86 are electrically connected and the circuits are functioning properly. As shown in FIG. 10(c), when the location procedure is completed, the magnetic rods 52 of the of the pointing devices 50 do not contact the second conductive circuit 86 on the positioning plate 82, and thus the first conductive circuit 85 and the second conductive circuit 86 are an open circuit. For that reason, the first LED 102 is inactive and the second LED 103 on the other loop of the relay circuit 101 is active, which means that the drilling may proceed.

In conclusion, during the location procedure performed with the pinpoint apparatus, there are two factors to determine whether the location procedure is accomplished or not. (1) the activation of the light of the alarm device changes from the first LED 102 to the second LED 103; and (2) the alignment between the magnetic rods 52 and the alignment lines 44. In which, before the location procedure is accomplished, the angular deviations between the magnetic rods 52 and the alignment lines 44 can be seen clearly. Thus, the position and the angle of the pinpoint apparatus can be further adjusted according to the direction indicated by the pointing devices 50.

Figure 11A:
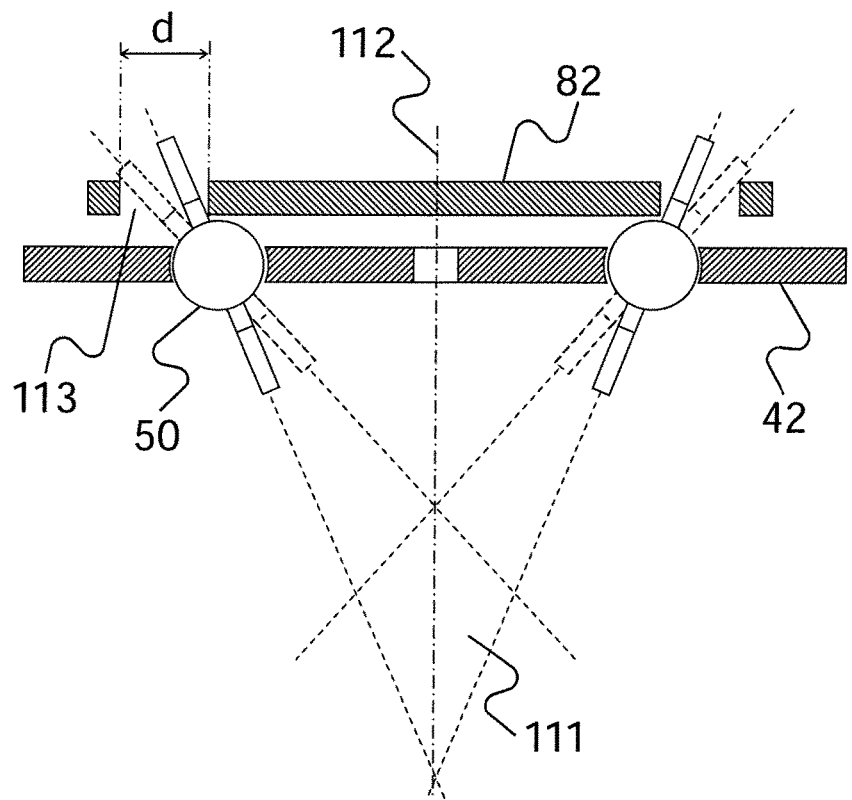
FIGS. 11A to 11B show the implementation of adjusting the location accuracy of the positioning plate.
Figure 11B:
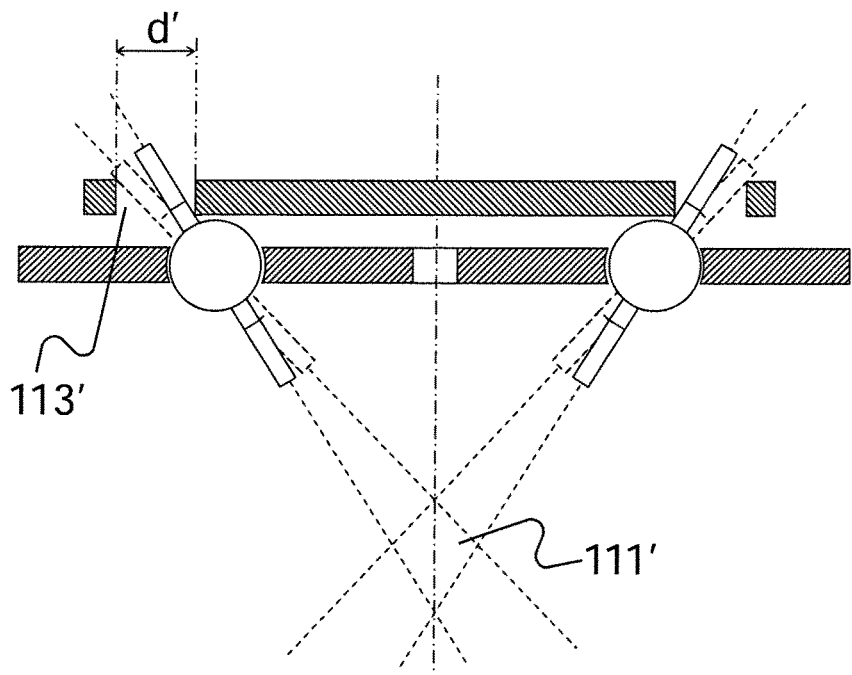

The alarm device has the function to turn on the alarm and the positioning plate cooperating with the alarm device has the function to adjust the accuracy of the pinpoint apparatus. As shown in FIGS. 11(a) and 11(b), the intersection 111 (or 111') is defined by the swing range of each magnetic rod 52, which is the possible location space of the intramedullary nail locking hole 12. The size of the location space is limited by the diameter of the positioning through hole 113 (or 113'). In the situation shown in FIG. 11(a), the diameter d of the positioning through hole 113 is larger, and thus the intersection 111 is larger. In the situation shown in FIG. 11(b), the diameter d' of the positioning through hole 113' is smaller, and thus the intersection 111 is narrower, and the accuracy of the pinpoint apparatus is increased.

Figure 12A:
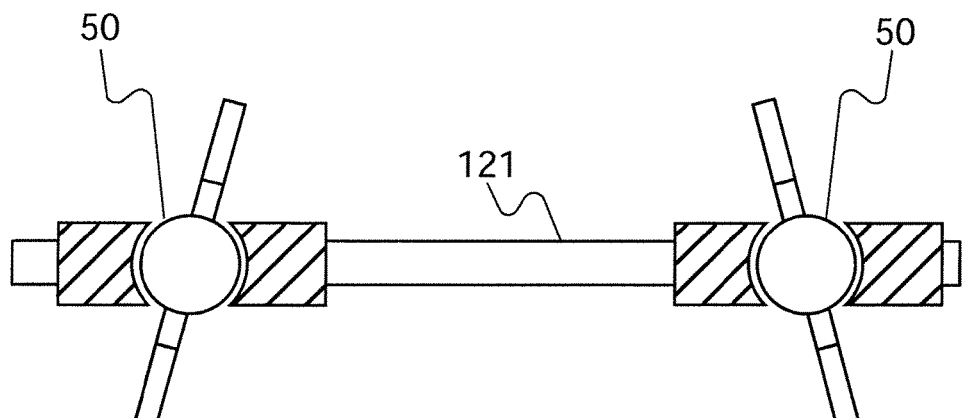
FIGS. 12A to 12B show the configuration of the pointing devices to calibrate the minimum distance between them.
Figure 12B:
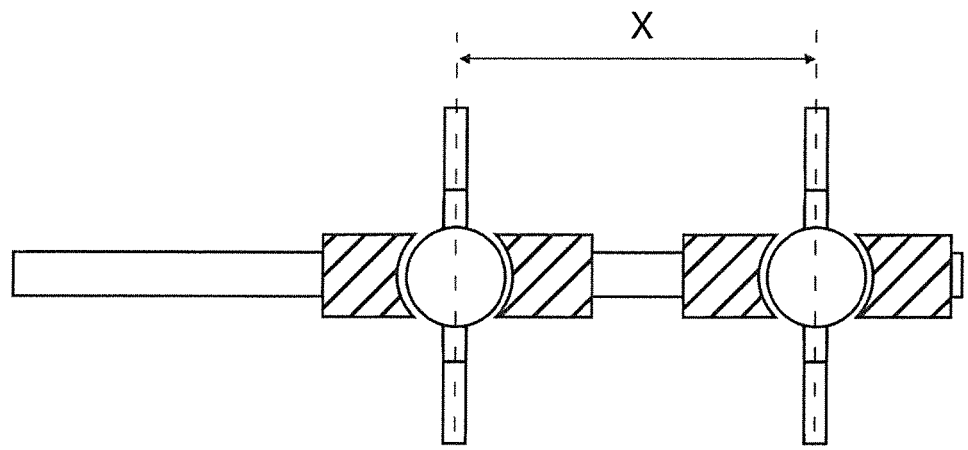

There are three pointing devices in the present invention, wherein each pointing device has a magnetic rod 52. To avoid the interference between the magnetic rods 52 of the pointing devices 50, the horizontal distance without interference with one another between two pointing devices has to be measured and calibrated. The setting of two pointing devices during the measurement is shown as FIGS. 12(a) and 12(b). Two pointing devices 50 are set on the test platform 121, in which the pointing devices 50 can horizontally slide on the test platform 121 and the magnetic directions of both the pointing devices 50 are the same. For example, both magnetic north poles of the pointing devices 50 are up. Following this, the pointing devices 50 are separated from each other far enough to avoid the interference of their magnetic fields, and the top ends of the pointing devices 50 are set as pointing to each other as much as possible. In the next step, the pointing devices 50 are pushed closer to each other. When the top end of the magnetic rods 52 of the pointing devices 50 are repel to each other as shown in FIG. 12(b), the distance X between the pointing devices 50 and 50' is measured and recorded.

Figure 13:
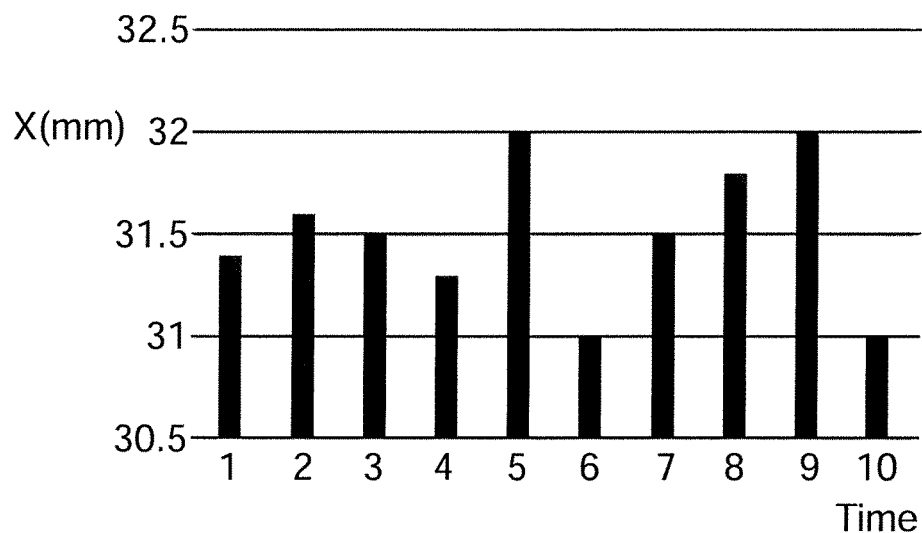
FIG. 13 is the calibration result of the minimum distance between the pointing devices.

The results of ten measurements are charted in FIG. 13. The results show that the effective horizontal distance of the repelling forces between the magnetic rods 52 of the pointing devices 50, in which the minimum effective horizontal distance is 32 mm. This means that there is no interference between the magnetic rods 52, when the pointing devices 50 and 50' are separated from each other more than at least this distance.

The accuracy of the present invention was verified by location accuracy measurements which include the horizontal accuracy measurement and angular accuracy measurement.

In the condition that the magnetic material 21 circling around the locking hole 12 is parallel to the pinpoint apparatus, the horizontal accuracy measurement verified the horizontal accuracy when the location procedure is accomplished. The pinpoint apparatus is fixed, the double alarm device is turned on, and magnetic material 21 is placed far away from the pinpoint apparatus as shown in FIG. 10(a). At this time, the first LED 102 is active, and then, the magnetic material 21 is moved to get close to the position directly below the sight hole 43. When the first LED 102 is inactive, the second LED 103 is active, all the magnetic rods 52 align with the alignment lines 84 (or 44), and the horizontal distance Xp between the center of the pinpoint apparatus and the magnetic material 21 is recoded. After that, the magnetic material 21 is moved away from the pinpoint apparatus through the projection of the sight hole 43 to the opposite direction. When the first LED 102 is active and the second LED 103 is inactive, the horizontal distance Xp between the center of the pinpoint apparatus and the magnetic material 21 is recoded again.

Figure 14:
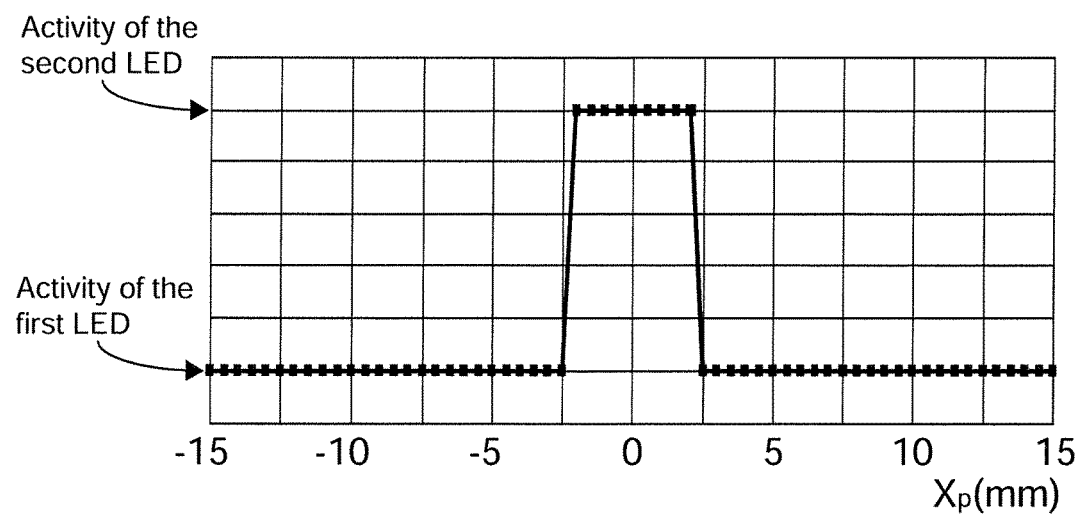
FIG. 14 is the calibration result of the horizontal accuracy of the pinpoint apparatus.

The results are plotted as FIG. 14. The results show that when the height between magnetic material 21 and the pinpoint apparatus is 16~20 mm, the error value of the horizontal accuracy is less than 2.1 mm.

When the magnetic material 21 circling around the locking hole 12 is roughly aligned to the sight hole 43 of the pinpoint apparatus as shown in FIG. 7(b), the angular accuracy measurement is used to determine the angular accuracy based on the angle of dip of the magnetic material 21 as the location procedure is accomplished.

Figure 15:
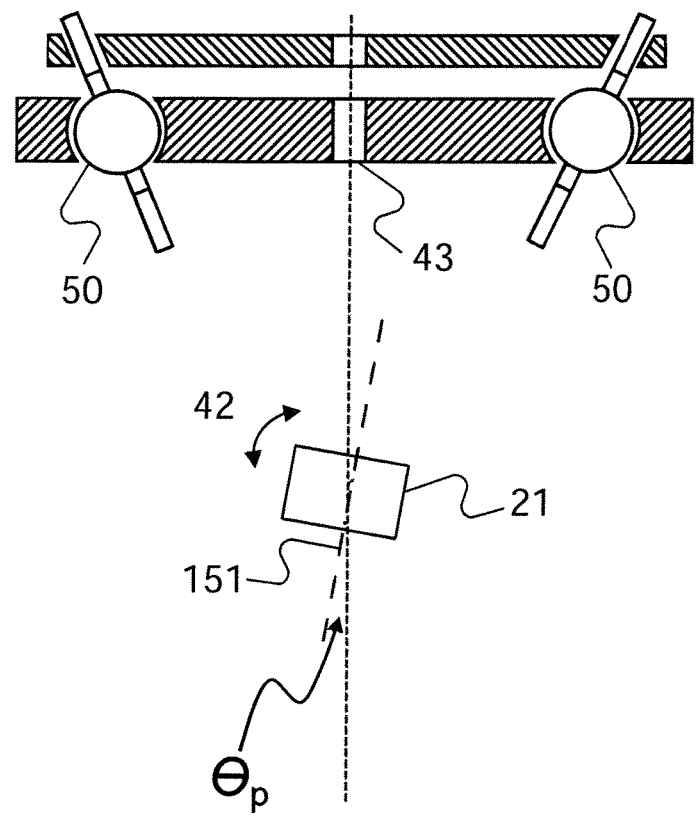
FIG. 15 shows the configuration of the pinpoint apparatus when calibrating the angle accuracy of the pinpoint apparatus.
Figure 16:
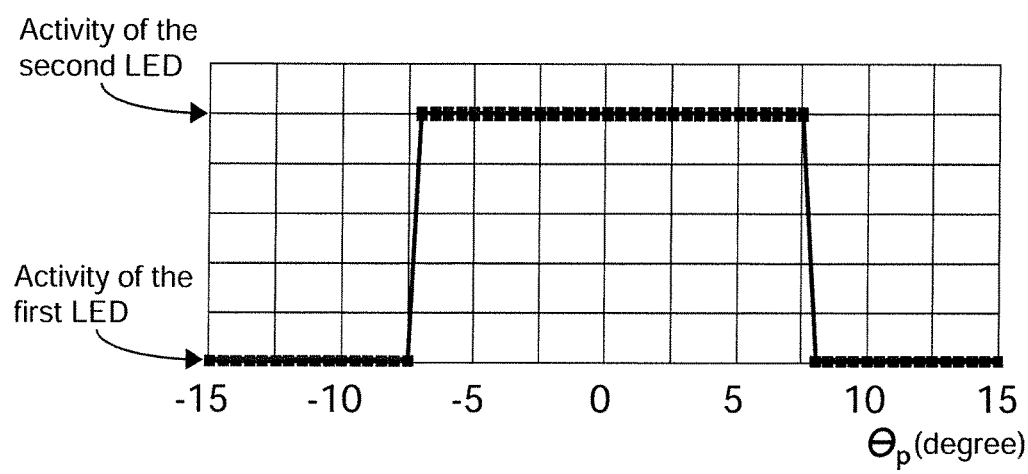
FIG. 16 is the calibration result of the angle accuracy of the pinpoint apparatus.

As shown in FIG. 15, the magnetic material 21 used to circle the intramedullary nail locking hole 12 is fixed on an rotational platform which can rotate along the direction 153 with respect to a horizontal axis and the double alarm device (not shown) is turned on. In the initial state of the angular accuracy measurement, the central axis 151 of the magnetic material 21 is set as vertical to the central axis 152 of the pinpoint apparatus, and the first LED 102 is active at that time. The rotational platform is rotated to make the central axis 151 to be superimposed on the central axis 152. When the first LED 102 is inactive, the second LED 103 is active and all the magnetic rods 52 of three pointing devices 50 align with the alignment lines 84 (or 44), the included angle θp between the central axis 151 and central axis 152 is recorded. Then, the rotation continues till the first LED 102 is active and the second LED 103 is inactive. At this time, the included angle θp between the central axis 151 and central axis 152 is recorded again. The included angle θp is equal to the angle of dip of the magnetic material 21. The results are plotted in FIG. 16. The results show that the error value of the angular accuracy is less than 7 degrees when the vertical distance between the magnetic material 21 and the pinpoint apparatus is 16~20 mm.

Tibias form pigs were used to perform the drilling test as follows. First, the approximate area of the magnetic material 21 circling the intramedullary nail locking hole 12 was located with the preliminary location apparatus, and then the position and the orientation of the intramedullary nail locking hole 12 was determined with the pinpoint apparatus. After the location procedure was completed, the additional fastening mechanism was applied to fasten the pinpoint apparatus, and the drilling was performed. The time to locate, the time to drill and whether the drill passed through the intramedullary nail locking hole 12 inside the pig tibia were recorded.

Each of two different operators performed the drilling test 5 times, and results are in the following table. The drill passed through the intramedullary nail locking hole 12 every time. The time to perform the stage-one location was 4~10 sec, the time to perform the stage-two location was 32~238 sec and the time to perform the entire location procedure was 36~248 sec, which is less than 5 min. The time to drill was 29~295 sec. The total of the time to drill plus the time to perform the entire location procedure is 109~450 sec, which is less than 8 min.

Results of the drilling test of the pig tibia:

| Test No. | Stage-one location | Stage-two location | Drilling | Total |
|---|---|---|---|---|
| The first operator | | | | |
| 1 | 8 | 238 | 204 | 450 |
| 2 | 5 | 185 | 78 | 268 |
| 3 | 5 | 109 | 49 | 163 |
| 4 | 4 | 102 | 81 | 187 |
| 5 | 9 | 114 | 217 | 340 |
| The second operator | | | | |
| 1 | 10 | 32 | 160 | 202 |
| 2 | 9 | 93 | 108 | 210 |
| 3 | 5 | 51 | 53 | 109 |
| 4 | 6 | 169 | 29 | 204 |
| 5 | 10 | 97 | 295 | 402 |

Unit: second

Figure 17A:
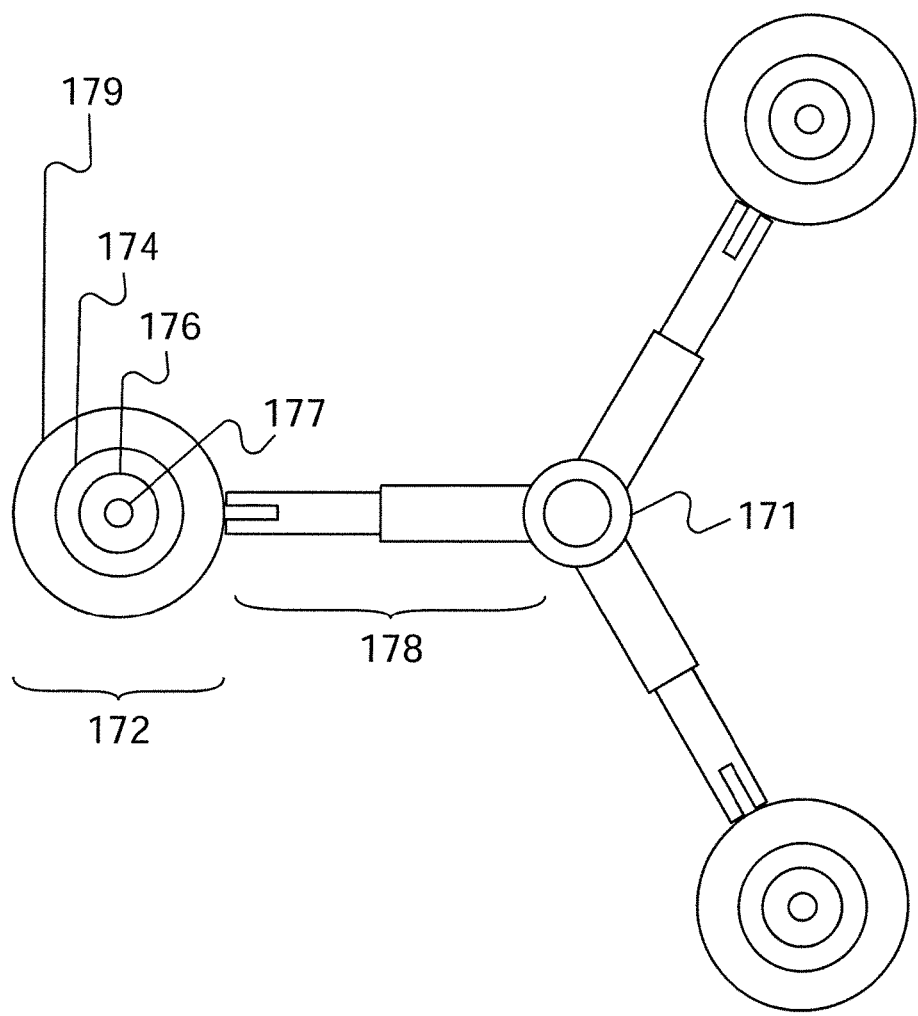
FIGS. 17A to 17C show another embodiment of the pinpoint apparatus of the present invention.
Figure 17B:
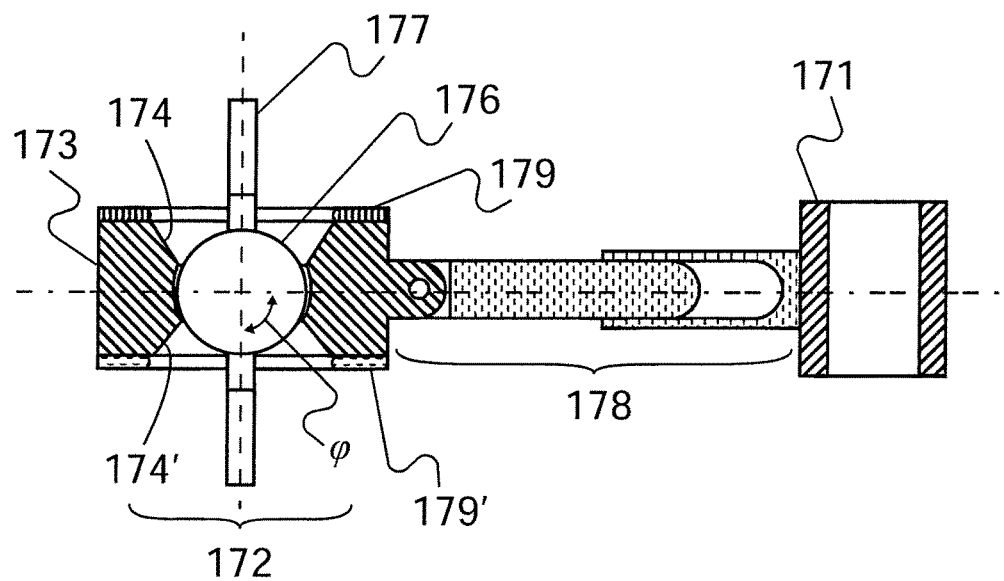
Figure 17C:
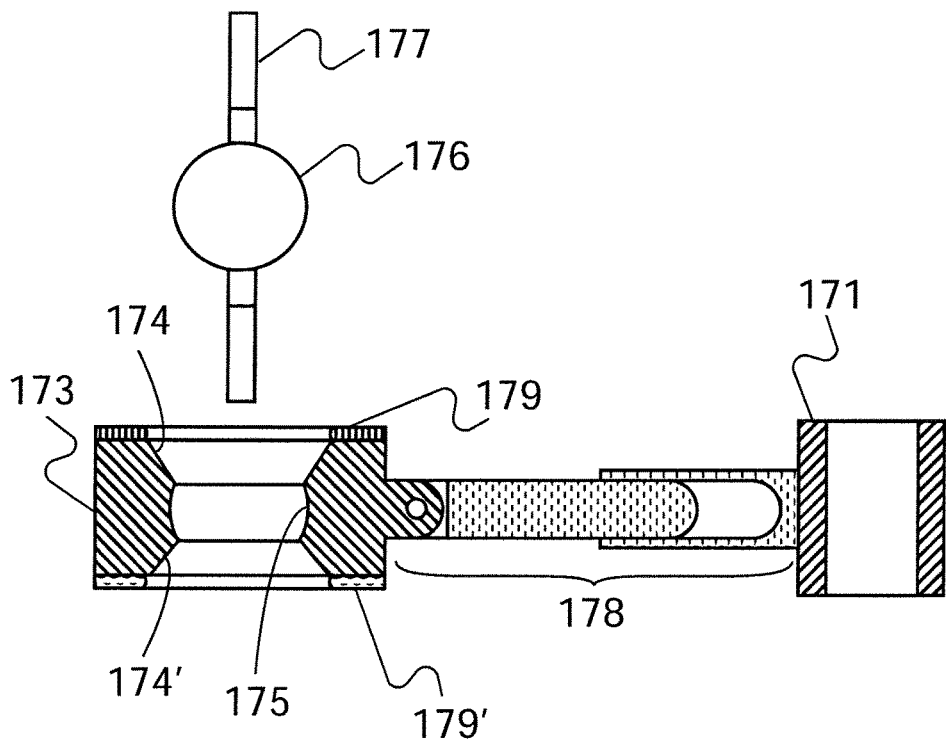

As shown in FIG. 17, the concept of the present invention can also be implemented with a magnetic location apparatus having the following structure, which includes: (a) an positioning ring 171; (b) a plurality of magnetic pointing device 172 separated from one another by the same distance, wherein each of which includes (b1) a ball-joint bearing portion 173 having (b11) a through hole which has two entrances 174 and 174' on the surface of the ball-joint bearing portion 172, penetrates the ball-joint bearing portion 172 and has a symmetric axis, and (b12) a ball-like space 175 which is inside the ball-joint bearing portion 173 having a center superimposed on the symmetric axis; and (b2) a ball-joint embedded portion having (b21) a ball-like body 176 embedded in the ball-like space 175 and (b22) a magnetic rod 177 which is connected to the ball-like body 176 passing through both of the entrances 174 and 174'; and (c) a plurality of connecting shafts 178, each of which has one end to connect to the positioning ring 171 and the other end portion to vertically pivot only one ball-joint bearing portion 173.

In which, each ball-joint embedded portion is made up of conductors and each ball-joint embedded portion further includes two conductive rings 179 and 179' disposed along the two entrances 174 and 174' and an alarm device electrically coupled to the two conductive rings 179 and 179'.

Furthermore, each connecting shaft 178 can be composed of a stretchable sleeve joint. Thus, each distance between each of the magnetic pointing devices and the positioning ring can be modified to fit various surgical situations.

All the measurements and calibrations mentioned above are suitable to this embodiment. However, in this embodiment, the suitable angle of dip to every ball-joint embedded portion 173 and the suitable length of every connecting shaft 178 is determined in advance and correspondingly the desired range of the inclination angle φ of every magnetic rod 177 is set.

Comparing FIG. 17 and FIG. 8, it can be seen that the two conductive rings 179 and 179' are functionally equivalent to the first conductive circuit 85 and the second conductive circuit 86, and the ball-joint embedded portion is functionally equivalent to the pointing device 50.

The main difference between this embodiment and the embodiments mentioned above is that the angle of dip for each ball-joint embedded portion can be adjusted during the location procedure. Therefore, the angle of dip for each ball-joint embedded portion can be used to limit the range of the inclination angle φ of each magnetic rod 177. This change can be carried out easily even during the location procedure in the surgery. In other embodiments, the range of the inclination angle of each pointing device 50 has to be limited by the positioning through hole 80 of the positioning plate 82. Change of the range of the inclination angle of each pointing device 50 means that the surgery has to be interrupted to change to a different positioning plate. Thus, the convenience when the configuration of this apparatus has to be changed is the clearest advantage of this embodiment.

Embodiments

1. A magnetic targeting apparatus, comprising: (A) a transparent bearing plate having a top surface, a bottom surface, and three containing through holes equally distant from one another extending from the top surface to the bottom surface, each of which is divided into an upper section, a lower section, and a middle section having a diameter larger than that of the lower section, and three pointing devices, each of which includes: (A1) a spherical embedded portion disposed in the middle section of the respective containing through hole; (A2) a first pointing end having one magnetic pole, passing through the upper section of the respective containing through hole, and connected to the spherical embedded portion; (A3) a second pointing end having the other magnetic pole, passing through the lower section of the respective containing through hole, coaxial with the first pointing end, and connected to the spherical embedded portion; and (A4) a conductive layer covering the spherical embedded portion, the first pointing end and the second pointing end; (B) a first conductive circuit disposed on the transparent bearing plate and electrically coupled to the conductive layer; and (C) a transparent positioning plate disposed on the transparent bearing plate in parallel, having three positioning through holes and including: (C1) a height adjuster adjusting a height as measured from the transparent bearing plate to the transparent positioning plate; (C2) three hole walls defining the three positioning through holes, which correspond to the three containing through holes respectively, and each of which passes therethrough one of the first pointing ends and the second pointing ends; and (C3) a second conductive circuit having three tubular conductors electrically coupled to one another and disposed on the three hole walls.

2. The magnetic targeting apparatus of Embodiment 1, wherein the transparent positioning plate is disposed on the top surface of the transparent bearing plate.

3. The magnetic targeting apparatus of any one of Embodiments 1-2, wherein the transparent bearing plate has a through sight hole extending from the top surface to the bottom surface, and equally distant from the three containing through holes; and the transparent positioning plate has a corresponding through sight hole coaxial with the sight hole.

4. The magnetic targeting apparatus of any one of Embodiments 1 to 3, wherein when compared to a respective containing through hole, the respective positioning through hole has a center more distant from that of the corresponding sight hole.

5. The magnetic targeting apparatus of any one of Embodiments 1 to 4, wherein the distance is a radius of the spherical embedded portion.

6. The magnetic targeting apparatus of any one of Embodiments 1 to 5, further comprising a voltage/current source electrically coupled to the first conductive circuit and the second conductive circuit.

7. The magnetic targeting apparatus of any one of Embodiments 1 to 6, further comprising an alarm device electrically coupled to the first conductive circuit and the second conductive circuit, and emitting signals according to one of a current change and a voltage change between the first conductive circuit and the second conductive circuit.

8. The magnetic targeting apparatus of any one of Embodiments 1 to 7, wherein the signals are sounds having different frequencies.

9. The magnetic targeting apparatus of any one of Embodiments 1 to 8, wherein the signals are lights having different colors.

10. The magnetic targeting apparatus of any one of Embodiments 1 to 9, further comprising: an intramedullary nail having a locking through hole; and a ring-like magnetic material circling and coaxial with the locking through hole and having a ring-like pole magnetically coupled to one of the first pointing end and the second pointing end.

11. A magnetic targeting apparatus, comprising: (A) a bearing component having a first surface, a second surface opposite to the first surface, and three containing through holes extending from the first surface to the second surface; and (B) three pointing devices, each of which comprises: (B1) a spherical portion embedded in the respective containing through hole; (B2) a first pointing end having a first magnetic pole and protruding from the spherical portion to the first surface; and (B3) a second pointing end having a second magnetic pole and protruding from the spherical portion to the second surface.

12. The magnetic targeting apparatus of Embodiment 11, further comprising: a positioning plate disposed on the bearing component and having three positioning through holes, wherein the three positioning through holes correspond to the three containing through holes to allow the first pointing ends and the second pointing ends to pass through.

13. The magnetic targeting apparatus of any one of Embodiment 11 and 12, wherein the bearing component and the three pointing devices are electrically coupled to one another to form a first conductive circuit.

14. The magnetic targeting apparatus of any one of Embodiments 11 to 13, further comprising three conductive rings, wherein each of the three positioning through holes has an opening, each of the three conductive rings is disposed around the opening, and the three conductive rings are electrically coupled to one another to form a second conductive circuit.

15. The magnetic targeting apparatus of any one of Embodiments 11 to 14, further comprising an alarm device electrically coupled to the first conductive circuit and the second conductive circuit, and emitting signals according to conductive conditions between the first conductive circuit and the second conductive circuit.

16. The magnetic targeting apparatus of any one of Embodiments 11 to 15, wherein the signals are sounds having different frequencies.

17. The magnetic targeting apparatus of any one of Embodiments 11 to 16, wherein the signals are lights having different colors.

18. A magnetic targeting apparatus, comprising: (A) a positioning ring having an exterior surface; (B) a plurality of pointing devices coplanar with the positioning ring, each of which comprises: (B1) a ball-joint bearing portion having a through hole with a symmetrical axis, and a ball-like space having a center located on the symmetrical axis; and (B2) a ball-joint embedded portion which has a ball-like body embedded in the ball-like space and a magnetic rod passing through the through hole; and (C) a plurality of connecting shafts, each of which has a first end connected to the positioning ring and a second end pivotally connected with the respective pointing device.

19. The magnetic targeting apparatus of Embodiment 18, wherein the first end has a connecting end connected to the positioning ring, and an opposite containing end having a blind hole extended toward the positioning ring, and the second end portion has a joint end pivotally connected with the pointing device, and a sleeving end which fits inside and can move within the blind hole.

20. The magnetic targeting apparatus of any one of Embodiments 18 and 19, wherein the through hole has two ends, and each of the plurality of pointing devices is conductive and further comprises: two conductive rings disposed around the two ends of the through hole respectively; and an alarm device electrically coupled to the two conductive rings and triggered by a conductive condition between the two conductive rings.

While the invention has been described in terms of what is presently considered to be the most practical and preferred Embodiments, it is to be understood that the invention needs not be limited to the disclosed Embodiments. On the contrary, it is intended to cover various modifications and similar arrangements included within the spirit and scope of the appended claims, which are to be accorded with the broadest interpretation so as to encompass all such modifications and similar structures.

What is claimed is:

1. A magnetic targeting apparatus for locating a locking hole of an intramedullary nail, comprising:
   a bearing plate having a centrally disposed sight hole, three containing through holes encircling the sight hole, and three alignment lines corresponding to the three containing through holes, respectively; and
   three pointing devices, the pointing devices configured to point to a magnetic material circling the locking hole of the intramedullary nail, each of the pointing devices comprising:
      a spherical portion embedded in the respective containing through hole;
      a first pointing end having a first magnetic pole and protruding from the spherical portion to a top surface of the bearing plate; and
      a second pointing end having a second magnetic pole and protruding from the spherical portion to a bottom surface of the bearing plate; wherein
   the three spherical portions are freely rotatable respectively in the three containing through holes to align each pointing device with the respective alignment line when the sight hole is coaxial with the locking hole.

2. The magnetic targeting apparatus of claim 1, further comprising a positioning plate disposed above the top surface of the bearing plate and having three positioning through holes, wherein a height adjuster is positioned between the positioning plate and the top surface of the bearing plate and the three positioning through holes correspond to the three containing through holes respectively to each pass therethrough a respective one of the first pointing ends.

3. The magnetic targeting apparatus of claim 2, wherein the bearing plate and the three pointing devices are electrically coupled to one another to form a first conductive circuit.

4. The magnetic targeting apparatus of claim 3, further comprising three conductive rings, wherein each of the three positioning through holes has an opening, each of the three conductive rings is disposed around the respective opening, and the three conductive rings are electrically coupled to one another to form a second conductive circuit.

5. The magnetic targeting apparatus of claim 4, further comprising an alarm device electrically coupled to the first conductive circuit and the second conductive circuit, wherein the alarm device emits signals according to conductive conditions between the first conductive circuit and the second conductive circuit.

6. The magnetic targeting apparatus of claim 5, wherein the signals are sounds having different frequencies.

7. The magnetic targeting apparatus of claim 5, wherein the signals are lights having different colors.

* * * * *